US006558685B1

(12) United States Patent
Kober et al.

(10) Patent No.: US 6,558,685 B1
(45) Date of Patent: May 6, 2003

(54) METHOD FOR TREATING WOOD AGAINST THE ATTACK OF HARMFUL FUNGI

(75) Inventors: Reiner Kober, Fussgönheim (DE); Adolf Parg, Bad Dürkheim (DE); Uwe Kardorff, Mannheim (DE); Reimer Göttsche, Baden-Baden (DE)

(73) Assignee: Dr. Wolman GmbH, Sinzheim (DE)

( * ) Notice: Subject to any disclaimer, the term of this patent is extended or adjusted under 35 U.S.C. 154(b) by 0 days.

(21) Appl. No.: 09/743,928

(22) PCT Filed: Jul. 14, 1999

(86) PCT No.: PCT/EP99/04968

§ 371 (c)(1),
(2), (4) Date: Jan. 17, 2001

(87) PCT Pub. No.: WO00/05955

PCT Pub. Date: Feb. 10, 2000

(30) Foreign Application Priority Data

Jul. 28, 1998 (DE) .......................... 198 34 028

(51) Int. Cl.$^7$ ................................ A01N 25/02
(52) U.S. Cl. ................ 424/405; 424/406; 504/116; 504/126; 504/130; 504/133; 504/134; 504/135; 504/138; 504/139; 504/140; 514/394; 514/395
(58) Field of Search ................ 514/394, 395; 424/405, 406; 504/116, 126, 130, 133–135, 134–140

(56) References Cited

U.S. PATENT DOCUMENTS

| 4,079,062 A | 3/1978 | VanReet |
| 4,532,341 A | 7/1985 | Holmwood |
| 5,013,748 A | 5/1991 | Radtke |
| 5,074,905 A | 12/1991 | Frisch |
| 5,106,848 A | 4/1992 | Seele |
| 5,672,954 A | 9/1997 | Watanabe |
| 6,074,986 A * | 6/2000 | Mulgreen et al. ........... 504/116 |

FOREIGN PATENT DOCUMENTS

| DE | 26 56 747 | 6/1978 |
| EP | 040 345 | 11/1981 |
| EP | 52 424 | 5/1982 |
| EP | 72 156 | 2/1983 |
| EP | 131 684 | 1/1985 |
| EP | 261 492 | 3/1988 |
| EP | 389 356 | 11/1988 |
| EP | 393 746 | 10/1990 |
| EP | 425 857 | 5/1991 |
| EP | 555 186 | 8/1993 |
| GB | 1591267 | 6/1981 |
| WO | 88/06841 | 9/1988 |
| WO | 95/01722 | 1/1995 |
| WO | 95/16349 | 6/1995 |
| WO | 95/16350 | 6/1995 |
| WO | 97/39865 | 10/1997 |

* cited by examiner

Primary Examiner—Neil S. Levy
(74) Attorney, Agent, or Firm—Keil & Weinkauf

(57) ABSTRACT

A multi-phase suspoemulsion containing as essential components a) 1 to 50% by weight of particular fungicidal benzimidazoles or precursors liberating them as microsuspended solids particles, b) 5 to 60% by weight of an emulsion comprising a fungicidal ingredient ($b_1$) and, in combination with ($b_1$), at least one component ($b_2$) or ($b_3$), in a water diluted form is useful to protected timber against fungal timber pests; ($b_1$) represents the fungicidal compounds fenpropimorph, fenpropidin, tridemorph, aldimorph and spiroxamine, ($b_2$) represents particular azole fungicides, and ($b_3$) represents particular benzoic esters.

6 Claims, No Drawings

METHOD FOR TREATING WOOD AGAINST THE ATTACK OF HARMFUL FUNGI

The present invention relates to multi-phase aqueous suspoemulsions and to their use for the treatment of timber against attack by fungal timber pests.

The fungicidal action of fenpropimorph (4-[3-{4-tert-butylphenyl}-2-methylpropyl]-2,6-cis-dimethylmorpholine) is generally known (cf. DE-A 26 56 747).

It is furthermore known to employ triazole compounds in timber protection [propiconazole: U.S. Pat. No. 4,079,062; tebuconazole: EP-A 40 345 and EP-A 52 424; cyproconazole: EP-A 131 684 and EP-A 555 186].

WO-A 95/16349 discloses fungicidal mixtures and compositions comprising them for crop protection which comprise, as active ingredients, fenpropimorph and a triazole compound.

EP-A 72 156 discloses the synergistic action of a mixture of fenpropimorph and prochloraz against phytopathogenic fungi.

Synergistic mixtures of triazole compounds are also customary in the protection of timber [propiconazole+tebuconazole: EP-A 393 746].

DE-A 43 40 853 teaches a synergistic mixture for use in the protection of timber which, besides a copper compound and an alkanolamine, comprises a triazole compound and a further fungicide, for example fenpropimorph.

Furthermore, EP-A 425 857 discloses the synergistic action of a mixture of fenpropimorph and epoxiconazole against fungal pests of materials.

WO 97/39865 describes synergistic mixture of fenpropimorph and various triazoles for use in the protection of timber. The combination of such mixtures with benzimidazoles, or with precursors liberating them, is not described.

EP 707 445 describes suspoemulsions based on the triazole epoxiconazole for crop protection. However, the solvents used therein are only poorly suited to use in the protection of timber since they volatilize relatively rapidly, owing to their high vapor pressure, which may lead to destabilization of the oil phase or to breaking of the emulsion. In addition, most of the solvents stated in EP-A 707,745 suffer from odor problems in enclosed spaces if a use as timber treatment agent is considered.

Moreover, the treatment systems in crop protection and timber protection differ greatly in as far as, as a rule, aqueous crop protection spray mixtures as tank mixes only require that the emulsion remain stable over, as a rule, a few hours and that these tank mixes can additionally be applied with the aid of a stirrer. In the protection of timber, in contrast, aqueous treatment systems are meant to be stable over weeks and months. In this context, the emulsions, suspoemulsions or microemulsions utilized by the timber are typically made up with treatment concentrates which have been made up freshly with water without this allowing the stability of an immersion bath mix to be adversely affected.

In contrast to crop protection, aqueous emulsions, microemulsions or, for example, suspoemulsions used in the protection of timber are thus subject to quite different quality criteria so that prior-art solutions to application problems can be transferred from crop protection to the protection of timber in terms of inception only.

Formulations with carbendazim (BCM) as biocides, fungicides and timber preservatives have been described repeatedly in the literature. The problem with BCM is that virtually no water-insoluble solvents are known which are capable of dissolving BCM in high concentration and thus to stabilize it as emulsion or microemulsion together with surfactants. Water-soluble solvents, in contrast, would lead to the precipitation or crystallization of BCM after high dilution.

This can be circumvented firstly by using BCM salts, where protonation with mineral acids exploits the very weakly basic character of BCM. Thus, CA 97:51133 describes phosphoric acid salts of BCM. However, such BCM salts are quite unsuitable for practice conditions in high dilution, in particular when using weakly basic tap water, since deprotonation, crystal formation or precipitation of BCM would follow very rapidly, and BCM would then be present in the form of coarse particles around >>10 mm in size, in which case it is virtually no longer effective and sediments very rapidly.

Furthermore, low pH values are frequently responsible for corrosion of timber preservative application plants.

A further possibility is found in JP 03251507 by suppressing sedimentation or crystal growth of BCM by means of xanthans. However, this generally results in very high xanthan contents of approx. 0.2% based on the use concentration or the tank mix or immersion bath mix. Based on the finished formulation, however, the xanthans would have to be employed like the active ingredients in the 100 g range of the finished formulation. This is not possible technically since xanthan gum contents in the suspoemulsion concentrate starting at as little as approx. 0.2% cause extremely high viscosity and such formulations are no longer flowable and give more gel-like, or even solid, products which are entirely unsuitable for the process.

It is an object of the present invention to develop liquid formulations with high concentrations of active ingredients comprising carbendazim and active ingredients from the class of the morpholines, amines and/or cycloamines or triazoles which, when applied in the protection of timber as suspoemulsions, exhibit good storage stability of the suspoemulsion and good long-term stability of the aqueous use product. Another object is to dispense as far as possible with readily vaporizable and malodorous solvents which are a health hazard, in particular chlorinated solvents. A further object was to formulate the active ingredients in high concentrations.

The systems according to the invention were intended to identify timber preservation methods which are improved from the economical and ecological points of view.

We have found that this object is achieved in accordance with the invention by multi-phase aqueous suspoemulsions comprising, as essential components, a) 1 to 50% by weight of a fungicidal active ingredient from the class of the benzimidazoles or the precursors liberating them of the formulae I.1. to I.4 as microsuspended solids particles, methyl 1-(butylcarbamoyl)benzimidazol-2-ylcarbamate (I.1)

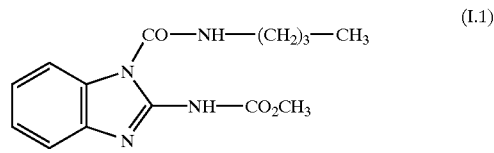

methyl benzimidazol-2-ylcarbamate (I.2)

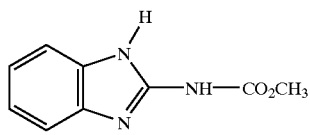

2-(2'-furyl)benzimidazole (I.3)

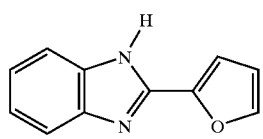

2-(1,3-thiazol-4-yl)benzimidazole (I.4)

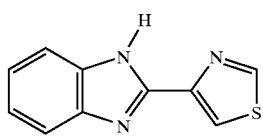

b) an emulsion comprising
  b₁) a fungicidal active ingredient selected from among compounds of the formulae II.1. to II.5 and

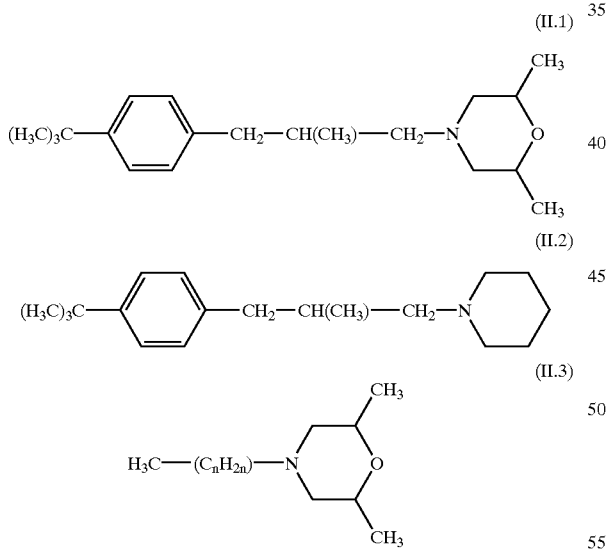

[n=10,11,12 (60–70%) or 13]

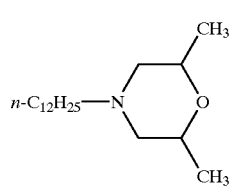

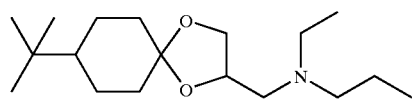

and, in combination with $b_1$), at least one component $b_2$) or $b_3$)

$b_2$) fungicidal active ingredients selected from among the azoles III.1. to III.18

1-[(2RS,4RS;2RS,4SR)-4-bromo-2-(2,4-dichlorophenyl)tetrahydrofuryl]-1H-1,2,4-triazole (III.1)

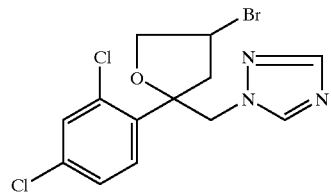

2-(4-chlorophenyl)-3-cyclopropyl-1-(1H-1,2,4-triazol-1-yl)butan-2-ol (III.2)

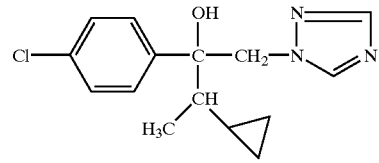

(±)-4-chloro-4-[4-methyl-2-(1H-1,2,4-triazol-1-ylmethyl)-1,3-dioxolan-2-yl]phenyl 4-chlorophenyl ether (III.3)

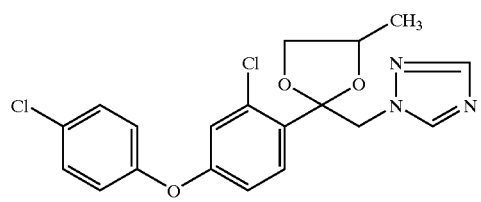

(E)-(R,S)-1-(2,4-dichlorophenyl)-4,4-dimethyl-2-(1H-1,2,4-triazol-1-yl)pent-1-en-3-ol (III.4)

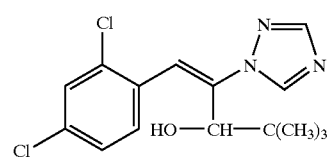

(Z)-2-(1H-1,2,4-triazol-1-ylmethyl)-2-(4-fluorophenyl)-3-(2-chlorophenyl)oxirane (III.5)

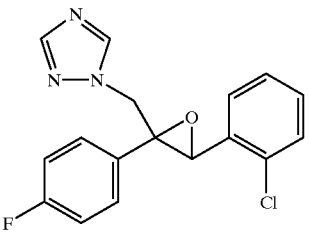

4-(4-chlorophenyl)-2-phenyl-2-(1H-1,2,4-triazolylmethyl)butyronitrile (III.6)

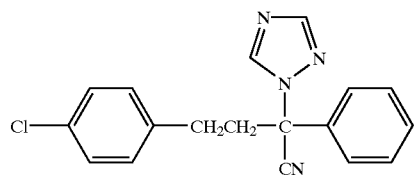

3-(2,4-dichlorophenyl)-6-fluoro-2-(1H-1,2,4-triazol-1-yl)quinazolin-4(3H)-one (III.7)

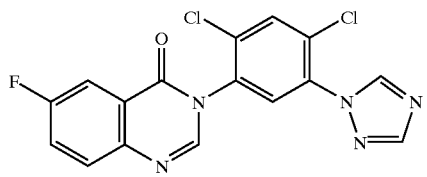

bis(4-fluorophenyl)(methyl)(1H-1,2,4-triazol-1-yl-methyl)silane (III.8)

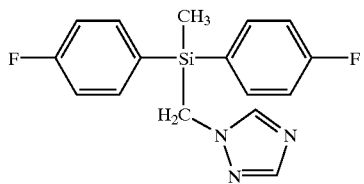

(R,S)-2-(2,4-dichlorophenyl)-1-(1H-1,2,4-triazol-1-yl)hexan-2-ol (III.9)

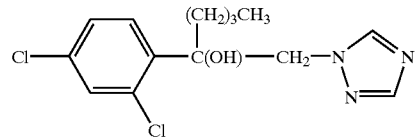

(1RS,5RS;1RS,5SR)-5-(4-chlorobenzyl)-2,2-dimenthyl-1-(1H-1,2,4-triazol-1-ylmethyl)cyclopentanol (III.10)

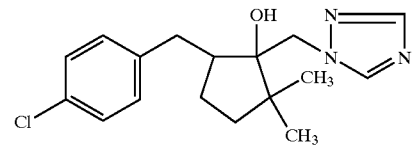

N-propyl-N-[2-(2,4,6-trichlorophenoxy)ethyl]-imidazole-1-carboxamide (III.11)

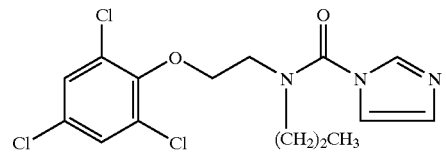

(±)-1-[2-(2,4-dichlorophenyl)-4-propyl-1,3-dioxolan-2-ylmethyl]-1H-1,2,4-triazole (III.12)

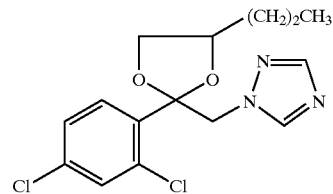

(R,S)-1-(4-chlorophenyl)-4,4-dimethyl-3-(1H-1,2,4-triazol-1-ylmethyl)pentan-3-ol (III.13)

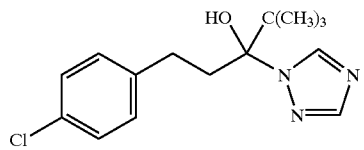

(±)-2-(2,4-dichlorophenyl)-3-(1H-1,2,4-triazol-yl)-propyl 1,1,2,2-tetrafluoroethyl ether (III.14)

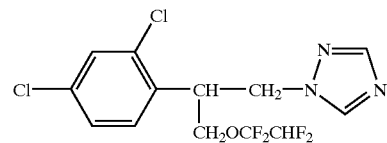

(E)-1-[1-[[4-chloro-2-(trifluoromethyl)phenyl]-imino]-2-propoxyethyl]-1H-imidazole (III.15)

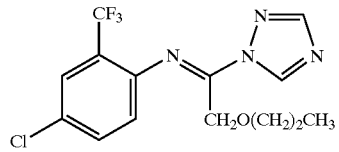

(RS)-2,4'-difluoro-α-(1H-1,2,4-triazol-1-ylmethyl)-benzhydryl alcohol (III.16)

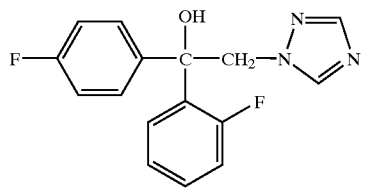

2-p-chlorophenyl-2-(1H-1,2,4-triazol-1-ylmethyl)-hexylnitrile

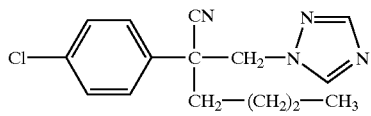

1-(2,4-dichloro-β-propylphenethyl)-1H-1,2,4-triazole (III.18)

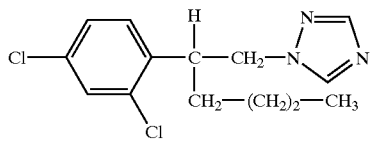

and/or
b₃) benzoic esters of the formula IV

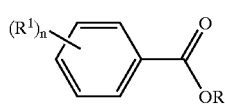

(IV)

where the substituents have the following meanings:
n has a value of 0 to 3
R is $C_1$–$C_8$-alkyl, $C_6$–$C_{14}$-aryl, $C_6$–$C_{14}$-aryl-$C_1$–$C_8$-alkyl,
$R^1$ is hydrogen, $C_1$–$C_8$-alkyl, $C_6$–$C_{14}$-aryl, $C_6$–$C_{14}$-aryl-$C_1$–$C_8$-alkyl-, halogen, $C_1$–$C_6$-alkoxy.

Preferred embodiments of the invention can be seen from the dependant claims.

Compounds I.1 to I.4 are known per se:

I.1 (common name: benomyl): U.S. Pat. No. 3,631,176, CAS RN [17804-35-2];

I.2 (common name: carbendazim): U.S. Pat. No. 3,657,443, CAS RN [10605-21-7];

I.3 (common name: fuberidazole): CAS RN [3878-19-1]; and

I.4 (common name: thiabendazol): U.S. Pat. No. 3,017,415, CAS RN [148-79-8].

Preferred as compound I is the active ingredient which is commercially available under the common name carbendazim.

The content of the compounds of the formula I is in the range of 1 to 50, preferably 5 to 30, in particular 10 to 20% by weight based on the total weight of the multi-phase suspoemulsion.

Component b (emulsion) generally amounts to 5 to 60, preferably 10 to 50, especially preferably 20 to 40% by weight of the multi-phase suspoemulsion.

The morpholine and piperidine derivatives II (II.1: common name: fenpropimorph, U.S. Pat. No. 4,202,894; II.2: common name: fenpropidin, U.S. Pat. No. 4,202,894; II.3: common name: tridemorph, DE-A 11 64 152), their preparation and their action against harmful fungi are also known. Compound II.4 is commercially available under the common name aldimorph and the trade name falimorph™. Compound II.5 is a novel fungicide (common name: spiroxamine) which is commercially available from Bayer under the names Accrue™, Torch™ or Impulse™.

The morpholine derivatives are generally present in an amount in the range of 20 to 90, preferably in the range of 45 to 75% by weight of emulsion b), based on the total weight of component b.

The azole derivatives III, their preparation and their action against harmful fungi is known per se:

III.1: common name: bromuconazole, Proc. Br. Crop Prot. Conf.-Pests Dis., 5-6, 439 (1990);

III.2: common name: cyproconazole, U.S. Pat. No. 4,664, 696;

III.3: common name: difenoconazole, GB-A 2,098,607;

III.4: common name: diniconazole, CAS RN [83657-24-3];

III.5: common name (proposed): epoxiconazole, EP-A 196 038;

III.6: common name: fenbuconazole (proposed), EP-A 251 775;

III.7: common name: fluquinconazole, Proc. Br. Crop Prot. Conf.-Pests Dis., 5-3, 411 (1992);

III.8: common name: flusilazole, Proc. Br. Crop Prot. Conf.-Pests Dis., 1, 413 (1984);

III.9: common name: hexaconazole, CAS RN [79983-71-4];

III.10: common name: metconazole, Proc. Br. Crop Prot. Conf.-Pests Dis., 5-4, 419 (1992);

III.11: common name: prochloraz, U.S. Pat. No. 3,991, 071;

III.12: common name: propiconazole, GB-A 1,522,657;

III.13: common name: tebuconazole, U.S. Pat. No. 4,723, 984;

III.14: common name: tetraconazole, Proc. Br. Crop Prot. Conf.-Pests Dis., 1, 49 (1988);

III.15: common name: triflumizole, JP-A 79/119,462

III.16: common name: flutriafole, CAS RN [76674-21-0]

III.17: common name: myclobutanil, CAS RN [88671-89-0]

III.18: Common name: penconazole, CAS RN [66246-88-6]

Triazole compounds which are particularly advantageously employed are propiconazole, penconazole, cyproconazole, hexaconazole, tebuconazole and mixtures of these.

The azole active ingredients III generally amount to 0 to 60, preferably 10 to 40, especially preferably 20 to 35% by weight of emulsion b).

The aromatic esters of the formula IV are benzoic acid derivatives known per se whose preparation is known per se to the skilled worker and has been described in the literature.

The benzyl esters of benzoic acid are preferred.

The compounds IV generally amount to 0 to 55, preferably 10 to 50, especially preferably 25 to 35% by weight of emulsion b).

The multi-phase suspoemulsions according to the invention may comprise, in emulsion b, mixtures of the active ingredients II with the aromatic esters of the formula IV, mixtures of the active ingredients II and the active ingredients of the formula III (preferred) or mixtures of compounds of the formula II, compounds of the formula III and compounds of the formula IV.

The term "timber" as used in the present context is also to be understood as including wood derivatives such as wood sections, wood pulps or other industrial products or else cellulose-containing materials which can be attacked by fungi, for examples intermediates in papermaking and lignified annual plants (bagasse, oilseed rape).

In general, the compounds II and the azole compounds III are present in the form of the free base. Typical pH values of a 1% strength aqueous treatment mixture are in the range of 6.5 to 9, preferably in the range of 7 to 8.

The components of emulsion b) should preferably have an oil phase density in the range of 0.95 to 1.05, preferably 0.975 to 1.025, g/cm$^3$ since this has an advantageous effect on the technical properties in use. The oil phase density can be controlled simply via the mixing ratio of the components in emulsion b); suitable data concerning the densities of the individual components are known to the skilled worker and described in the literature, so that more detailed information can be dispensed with here.

When using an especially advantageous combination of an active ingredient of the formula II, in particular fenpropimorph, and an active ingredient of the formula III, in particular propiconazole, hexaconazole and/or penconazole, a mixing ratio in the range of 1.5:1 to 5:1, in particular 2:1 to 4:1, has proved suitable and advantageous for establishing a suitable density.

An emulsion of fenpropimorph and propiconazole is especially preferably employed as component b.

The advantage of establishing the oil phase density at a value of as close to 1 g/cm$^3$ as possible is that creaming is largely prevented when the use concentration is later established by means of dilution. Moreover, the sedimentation behavior of the crystalline SC phase of the active ingredient I is improved. Finally, coalescence of the oil phase can also be prevented to a very large extent.

To adjust the oil phase density of the emulsion comprising the active ingredients of the formula II, the aromatic esters of the formula IV may also be improved in accordance with the invention instead of the azole compounds III. Triazoles are therefore not necessarily required for achieving the desired effect. As a rule, the benzoic ester content amounts to 30 to 200 g/l, preferably to a range of 50 to 150 g/l, based on the total formula of the formulation.

The multi-phase aqueous suspoemulsions according to the invention can be prepared in a manner known per se, for example by the methods described in EP-A 707,445, so that more detailed information can be dispensed with here.

In an individual case, the azole component III may also be present as suspension concentrate component (SC component) in mixture with a compound of the formula I, in particular when the melting point of the azole is above 100° C. while its solubility in active ingredients of the formula II or compounds of the formula IV is less than 10 g/l, in particular less than 2 g/l. An example of such an azole component which can be formulated advantageously as a mixture with, for example, carbendazim, is epoxiconazole.

The multi-phase aqueous suspoemulsions according to the invention can additionally comprise formulation auxiliaries which are known per se, besides the above-described components.

Suitable surfactants are the alkali metal, alkaline earth metal or ammonium salts of aromatic sulfonic acids, for example ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or of phenolsulfonic acid with formaldehyde, condensates of phenol with formaldehyde and sodium sulfite, polyoxyethylene octylphenol ether, ethoxylated isooctyl-, octyl- or nonylphenol, tributylphenyl polyglycol ether, alkylaryl polyether alcohols, isotridecyl alcohol, ethoxylated castor oil, ethoxylated triarylphenols, salts of phosphated triarylphenol ethoxylates, lauryl alcohol polyglycol ether acetate, sorbitol esters, lignosulfite waste liquors or methylcellulose, or mixtures of these.

When surfactants are also used, they generally amount to 0.5 to 25% by weight, based on the total weight of the suspoemulsion according to the invention.

Emulsifiers which can be used are nonionic, cationic and anionic emulsifiers. Quaternary ammonium compounds and alkoxylated, in particular ethoxylated, fatty alcohols, oxo alcohols and oils (castor oil, fish oil) are preferred.

Emulsifiers which have proved very especially advantageous are fatty amines alkoxylated with 2 to 25 moles of ethylene oxide, such as Ethomen® C 15, Ethomen® T23 or Ethomen® S20 (Akzo Chemicals GmbH, 52355 Düren, Germany).

To widen the spectrum of action or to achieve particular effects, for example additional protection against insects including termites, the abovementioned solvent-comprising formulations or emulsion concentrates can be combined with further active ingredients which, in the latter case, are incorporated together with suitable additional emulsifiers.

Suitable components in mixtures are, for example, the following compounds:

sulfenamides such as dichlofluanide, tolylfluanide, folpet, fluorfolpet;

benzimidazoles such as carbendazim, benomyl, fuberidazole, thiabendazole or their salts;

thiocyanates such as thiocyanatomethylthiobenzothiazole, methylene bisthiocyanate;

quaternary ammonium compounds such as benzyldimethyltetradecylammonium chloride, benzyldimethyldodecylammonium chloride, didecyldimethylammonium chloride;

quaternary phosphonium compounds;

iodine derivatives such as diiodomethyl p-tolyl sulfone, 3-iodo-2-propynyl alcohol, 4-chlorophenyl-3-iodopropargyl formal, 3-bromo-2,3-diiodo-2-propenyl ethyl carbonate, 2,3,3-triiodoallyl alcohol, 3-bromo-2,3-diiodo-2-propenyl alcohol, 3-iodo-2-propynyl n-butylcarbamate, 3-iodo-2-propynyl n-hexylcarbamate, 3-iodo-2-propynyl cyclohexylcarbamate, 3-iodo-2-propynyl phenylcarbamate, 0-1-(6-iodo-3-oxo-5-hexynyl) butylcarbamate, 0-1-(6-iodo-3-oxo-5-hexynyl) phenylcarbamate, napcocide;

phenol derivatives such as tribromophenol, tetrachlorophenol, 3-methyl-4-chlorophenol, dichlorophene, o-phenylphenol, m-phenylphenol, p-phenylphenol, 2-benzyl-4-chlorophenol;

bromine derivatives such as 2-bromo-2-nitro-1,3-propanediol, 2-bromo-2-bromomethylglutaronitrile;

isothiazolinones such as N-methylisothiazolin-3-one, 5-chloro-N-methylisothiazolin-3-one, 4,5-dichloro-N-octylisothiazolin-3-one, N-octylisothiazolin-3-one;

benzoisothiazolinones such as 4,5-trimethylisothiazol-3-one;

pyridines such as 1-hydroxy-2-pyridinethione (and their sodium, iron, manganese and zinc salts), tetrachloro-4-methylsulfonylpyridine;

metal soaps such as tin naphthenate, tin octanoate, tin 2-ethylhexanoate, tin oleate, tin phosphate, tin benzoate, copper naphthenate, copper octanoate, copper 2-ethylhexanoate, copper oleate, copper phosphate, copper benzoate, zinc naphthenate, zinc octanoate, zinc 2-ethylhexanoate, zinc oleate, zinc phosphate and zinc benzoate;

organotin compounds, for example tributyl tin (TBT) compounds, dialkyldithiocarbamates such as sodium and zinc salts of dialkyldithiocarbamates, tetramethylthiuram disulfide;

nitriles such as 2,4,5,6-tetrachlorisophthalonitrile;

benzothiazoles such as 2-mercaptobenzothiazole;

quinolines such as 8-hydroxyquinoline and their copper salts or quinoxyfen;

tris-N-(cyclohexyldiazeniumdioxy)aluminum, N-(cyclohexyldiazeniumdioxy)tributyltin or its potassium salt, bis-N-(cyclohexyldiazeniumdioxy)copper;

Insecticides which are preferably added are:

phosphoric esters such as azinphos-ethyl, azinphos-methyl, 1-(4-chlorophenyl)-4-(O-ethyl, S-propyl) phosphoryloxy-pyrazole, chloropyrifos, coumaphos, demeton, demeton-S-methyl, diazinon, dichlorvos, dimethoate, ethoprophos, etrimfos, fenitrothion, fenthion, heptenophos, parathion, parathion-methyl, phosalone, phoxim, pirimiphos-ethyl, pirimiphos-methyl, profenofos, prothiofos, sulfprofos, triazophos and trichloron;

organosilicon compounds, preferably dimethyl(phenyl) silylmethyl-3-phenoxybenzyl ethers such as dimethyl (4-ethoxyphenyl)silylmethyl-3-phenoxybenzyl ether or (dimethylphenyl)silylmethyl-2-phenoxy-6-pyridylmethyl ethers such as dimethyl-(9-ethoxyphenyl)silylmethyl-2-phenoxy-6-pyridylmethyl ether or (phenyl-3-(3-phenoxyphenyl)propyl) dimethylsilanes such as, for example, (4-ethoxyphenyl)-(3-(4-fluoro-3-phenoxyphenylpropyl)dimethylsilane;

pyrethroids such as allethrin, alphamethrin, bioresmethrin, byfenthrin, cycloprothin, cyfluthrin, decamethrin, cyhalothrin, cypermethrin, deltamethrin, α-cyno-3-phenyl-2-methylbenzyl 2,2-dimethyl-3-(2-chloro-2-trifluoromethylvinyl)cyclopropane carboxylate, fenpropathrin, fenfluthrin, fenvalerate, flucythrinate, flumethrin, fluvalinate, permethrin, resemethrin and tralomethrin;

nitroimines and nitromethylenes such as 1-((6-chloro-3-pyridinyl)methyl)-4,5-dihydro-N-nitro-1H-imidazol-2-amine (imidacloprid), N-((6-chloro-3-pyridyl)methyl)-N'-cyano-N'-methylacetamide;

molting inhibitors such as flurox and farox.

An addition to the suspoemulsions according to the invention of acids which are insoluble in water may also improve the efficacy of the active substances. Examples of suitable organic acids which are insoluble in water are aliphatic or aromatic mono- or polycarboxylic acids, for example, an aliphatic unbranched monocarboxylic acid with 5 to 20 C atoms such as hexanoic acid, heptanoic acid, octanoic acid, nonanoic acid and decanoic acid, or an aliphatic branched monocarboxylic acid with 5 to 20 C atoms such as 2-ethylpentanoic acid, 2-ethylhexanoic acid, 2-ethylheptanoic acid, isooctanoic acid, isononanoic acid and versatic acid, or neocarboxylic acid (monocarboxylic acids with a greater degree of branching), or an aliphatic dicarboxylic acid with 5 to 20 C atoms such as sebacic acid and decanedicarboxylic acid, or an aromatic or aralipathic carboxylic acid such as naphthenoic acid and benzoic acid.

Such acids are preferably employed as anions of metal salts, in particular of alkali or alkaline earth metals, if appropriate as copper salts, ammonium salts or organic ammonium salts derived from primary, secondary or tertiary amines or quaternary ammonium salts.

The aqueous multi-phase suspoemulsions according to the invention or their aqueous dilutions may additionally be admixed with binders, for example oil-soluble or water-dilutable alkyd resins, acrylate dispersions, or, in the case of primers which comprise approx. 2 to 10% by weight of solid resin or glazes which comprise approx. 10 to 25% of solid resin, else inorganic or organic pigment preparations, water- and oil-soluble colorants, water repellants such as metal stearates or waxes and/or other auxiliaries such as dryers, wetters and penetrants.

The use for protecting the timber can be carried out, for example depending on the degree of risk to the timber:
a) by spraying the timber with the dilute suspoemulsion,
b) by immersing the timber in the suspoemulsion (short-term immersion to vat immersion),
c) by painting or flooding the timber.

The concentration of the fungicidal mixture in the timber preservative in question depends in most cases on the degree to which the timber to be treated is at risk from the fungi and, in addition, on the application method chosen. In the case of wood derivatives and cellulose, for example, undilute concentrates are employed in most cases (for example in the case of plywood, chipboard, bagasse-board).

As a rule, the success of the treatment with the fungicidal mixtures or the ready-to-use timber preservatives, in particular with the suspoemulsions according to the invention, also depends on the application method.

When dilute systems are applied, they comprise, as a rule, 0.1 to 3%, preferably 0.3 to 1.5%, of the suspoemulsion according to the invention, the remainder being water or a mixture of water/organic solvent; water is preferred.

The mixtures and timber preservatives used in accordance with the invention protect particularly effectively against wood-discoloring fungi, in particular blueing fungi, and mainly *Aureobasidium pullulans* and *Sclerophoma pityophila*, which belong to the Ascomycetes.

In addition, it has been found that the mixtures and timber preservatives also effect good protection of timber against
a) Basidiomycetes (for example *Serpula lacrymans, Coniophora puteana*) and
b) other Ascomycetes such as molds (for example *Aspergillus niger*) and fungi which cause soft rot (for example *Chaetomium globosum*).

EXAMPLES

The suspoemulsions according to the invention with the formulas as shown in Tables 1a, 1b and 2 and use products can be prepared analogously to the procedure described in EP 707 445. Indications regarding properties of EC and SC formulations are also found in this publication. As a rule, the multi-phase systems described in EP 707 445 are also suspoemulsions composed of an aqueous phase, an oil phase (also termed EC phase) and an SC phase, as is the case with the formulations of the present invention.

The suspoemulsions according to the invention of Tables 1a, 1b and 2 hereinbelow were prepared by introducing an oil phase of the composition stated in the table into a suspension concentrate of the active ingredient carbendazim (I.2) with vigorous stirring or with vigorous dispersing or shearing, and suspoemulsifying it therewith.

1. Preparation of the carbendazim (BCM) suspension (BCM stock SC)

500 g of BCM (calc. 100% active ingredient) are stirred into 500 ml of distilled or fully demineralized water and 20 g of Pluronic PE 10500 and 20 g of Wettol D1 and the mixture is made up to 1 l. As specified in EP 707 445, Example 1, the mixture was then ground in a ball mill with cooling to 10° C. until a particle size of 80%<2 microns had been established.

Then, aliquots of this BCM stock suspension were employed for all suspoemulsions in accordance with the formulas hereinbelow.

2 General experimental description of the protocol for the preparation of suspoemulsions from BCM suspensions 2.1 Kelzan S was stirred in the residual amount of water (depending on the degree of purity of the active ingredients) which had been introduced into a reaction vessel until swelling was complete and a slightly viscous homogeneous mixture had been established (stirring time of approx. 2 hours).

2.2 Then, aliquots of the BCM stock suspension, Wettol D1;

1,2-propylene glycol; formaldehyde, Pluronic PE 10500 or other auxiliaries were subsequently added as per formula as further constituents and the mixture was stirred until the pulverulent Wettol D1 had dissolved completely and a homogeneous suspension had been established.

2.3 Then, a homogeneous mixture of morpholine and triazole, in this case fenpropimorph and propiconazole or benzoic ester were then added continuously, with continued stirring, in the relevant ratio as specified in the formulas of Tables 1a, 1b and 2, and stirring was continued for approx. 100 minutes using a dissolver stirrer.

2.4. The active ingredient contents were subsequently analyzed by sampling, and a particle size check was carried out.

2.5. Finally, Silicon SRE was added to make up the mixture to 1 l of suspoemulsion, with slow stirrer speed.

After steps 2.1. to 2.5. have been carried out, a particle size of the suspoemulsions according to the invention results where, as a rule, 40% are smaller than 2 microns and 100% smaller than 8 microns; if appropriate, afterdispersion may be carried out in order to achieve these values, which have proved advantageous.

The table hereinbelow illustrates the components employed in the examples:

TABLE 1

| Name | Chemical name | Supplier |
|---|---|---|
| Antischaunmittel SRE | Silicone oil emulsion | Wacker-Chemie |
| Pluronic ® PE 10500 | EO/PO block copolymer | BASF AG |
| Wettol ® D 1 | Condensate of phenolsulfonic acid, urea and formaldehyde | BASF AG |

The readymixes of Table 1a were diluted with tap water to 150 ml at concentrations of 0.7 and 2.8% and homogenized for 5 minutes using a magnetic stirrer. Then, calibrated 100 ml conical cylinders were filled completely and without inclusion of air with the dilute suspoemulsions, sealed with a stopper and placed with the calibrated conical end upward or upside-down with the stopper pointing downward.

After in each case 24 hours, creaming is read off in mm, the cylinders are subsequently shaken 30× or largely rehomogenized and again left to stand.

The compositions and the results can be found in Table 1a hereinbelow.

TABLE 1a

| Constituents of selected formulations: | Formulation Experiment No. 1a-1 (according to the invention) g/l | Formulation Experiment No. 1a-2 (Comparative) g/l |
|---|---|---|
| Carbendazim (BCM) | 90 | 90 |
| Fenpropimorph (FPM) | 270 | 270 |
| Wettol ™ D1 | 45 | 45 |
| Pluronict 10 500 | 17.4 | 17.4 |
| 1,2-Propylene glycol (antifreeze agent) | 34.7 | 34.7 |
| Benzyl benzoate (Aldrich) | 139.5 | |
| Silikonöl AP 500 (Wacker-Chemie) | | 139.0 |
| Oil phase density*: | approx. 1.0 g/ml | approx. 1.0 g/ml |
| Creaming (0.7% of the above mentioned formulations) | in ml | in ml |
| Immediately or within 0.5 hour | none | <0.1 |
| 24 hours | <0.05 | 0.25 |
| 72 hours | 0.10 | 0.45 |
| Creaming (2.8% of the above mentioned formulations) | in ml | in ml |
| 24 hours | <0.05 | 1.00 |

Determining the physical storage stability after 6 months by determining the content of particles with a particle size of less than 2 microns revealed a value of 46.5 and 51.1% (for 40 and 50° C., respectively) in the case of 1a-1, while the corresponding values for 1a-2 were 36.5 and 35.1%, respectively.

Both readymixes or suspoemulsions as shown in Table 1a comprise, as further inert constituents, additionally 1.8 g/l of the biocide Kathon™ MK, a commercial product from Rohm and Haas (Philadelphia) and 2.5 g/l of the antifoam Silicon SRE, a commercial product from Wacker-Chemie.

The mixture of components FPM/benzyl benzoate or FPM/Silikonöl AP 500 was determined as oil phase density.

Experimental Series Ib

Further comparative experiments with FPM and high-density auxiliaries were carried out analogously in accordance with the formulas of Table 1a in order to optimize the morpholine oil phase density. However, as can be seen from Table 1b, the resulting suspoemulsions proved to be physically totally unstable and unsuitable, in contrast to the suspoemulsions comprising benzoic esters or silicone oils, so that it was impossible to carry out long-term experiments on the storage stability or an experiment under use concentrations.

TABLE 1b

Oil phase densities: 0.99–1.01 g/ml according to contents:

| Experiment No. | FPM content g/l | Auxiliary content g/l | Assessment of the suspoemulsions |
|---|---|---|---|
| 1b-1 | 270 | 125.5 2-Phenyl-phenol | No dispersibility |
| 1b-2 | 270 | 118.5 Dimethyl phthalate | Flocculation and agglomeration of the readymix |
| 1a-1 | 270 | 139.0 Benzyl benzoate | In accordance with the invention see Experiment 1a-1; |

*The desired densities around 1.0 g/ml were established by iteratively mixing FPM with the components 2-phenylphenol or dimethyl phthalate.

Experimental Series II

The experiments were carried out as described for Experimental Series I.

Table 2 below contains information on auxiliaries and active ingredients in g/l with a 0.5% strength use concentration of the suspoemulsions, and results on creaming experiments in accordance with Table 1. The storage stabilities of the suspoemulsions employed are also described in the form of the particle sizes.

TABLE 2

Formulas (active ingredient contents as shown in Table 1 and auxiliaries in g/l in the tank mix/conical cylinder test) and storage stabilities and creaming behavior of the formulations:

| Active ingredient/ Auxiliary | Formulation 2a (Comparison 1) | Formulation 2b (Comparison 2) | Formulation 2c (According to the invention) |
|---|---|---|---|
| Carbendazim | 0.6 | 0.6 | 0.6 |
| Fenpropimorph | 1.8 | 1.8 | 1.0 |
| Propiconazole | — | — | 0.3 |
| Wettol ™ D 1 | — | 0.2 | 0.2 |
| Pluronic ™ PE 10500 | — | 0.3 | 0.03 |
| Oil phase density* | 0.93 (here: FPM) | 0.93 (here: FPM) | 0.99 |

| Creaming in ml after | Experiments in the conical cylinder as per Table 1 * | | |
|---|---|---|---|
| 24 h | 0.40 (1.40) | 0.25 (0.75) | <0.05 (no creaming) |
| 48 h | 0.45 (1.40) | 0.35 (0.90) | 0.05 (0.05) |
| 72 h | 0.55 (1.40) | 0.35 (1.15) | 0.10 (0.05) |

* In brackets: data obtained with a 2% use concentration;

Determining the formulation storage stability after 6 months by determining the content of particles with a particle size of less than 2 microns revealed a value of 47.6% at 40° C. and a value of 49.5% at 50° C. in the case of formulation 2. In the case of the suspoemulsion 2c according to the invention, the corresponding values were 57 and 60.1%, respectively.

All formulations of Table 2 comprise, as further inert auxiliaries, 0.2 g/l of 1,2-propylene glycol, 0.01 g/l of antifoam Silicon SRE (product of Wacker-Chemie GmbH) and 0.01 g/l of the biocide Kathon™ MK.

Compared with the prior-art formulations 2a and 2b, formulation 2c according to the invention provides marked improvement with regard to the creaming behavior at use concentrations.

Scale-up experiments on the 100-1-scale also revealed that formulations which were analogous to 2c remained homogeneous, highly reemulsifiable and thus reliable upon use.

The suspoemulsions according to the invention are generally employed as timber treatment product in a concentration of 0.1–3%, but preferably 0.3–1.5% strength in water.

The optimal application rate of the suspoemulsions varies depending on the risk of microbial contamination to which the timber is exposed. Thus, regional quantities and qualities of existing microorganisms and pathogens require an adapted application rate as a function of the treatment method and the average temperature of the conditions under which the timber is stored.

We claim:

1. A multi-phase aqueous suspoemulsion comprising, as essential components, a) 1 to 50% by weight of a fungicidal active ingredient from the class of the benzimidazoles or the precursors liberating them of formulae I.1. to I.4 as microsuspended solids particles, methyl 1-(butylcarbamoyl)benzimidazol-2-ylcarbamate (I.1)

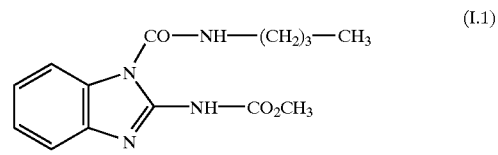

methyl benzimidazol-2-ylcarbamate (I.2)

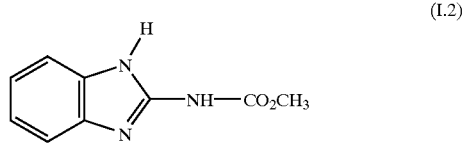

2-(2'-furyl)benzimidazole (I.3)

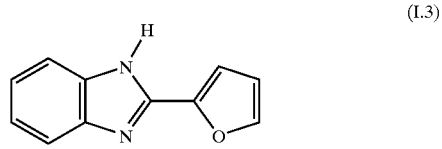

2-(1,3-thiazol-4-yl)benzimidazole (I.4)

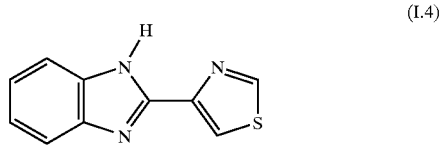

b) 5 to 60% by weight of an emulsion comprising
  $b_1$) a fungicidal active ingredient selected from among compounds of formulae I.1, to II.5

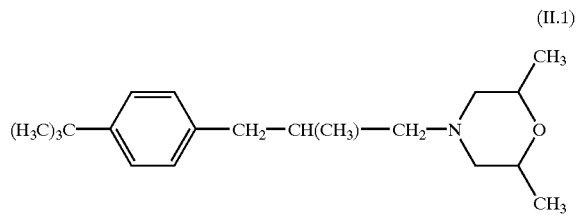

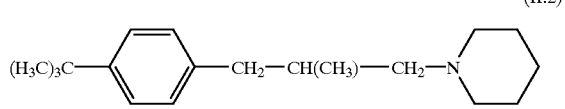

-continued

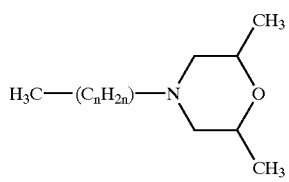

(II.3)

[n = 10, 11, 12 (60–70%), 13]

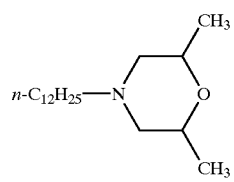

(II.4)

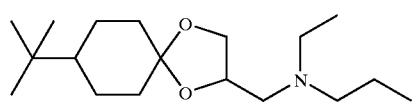

(II.5)

and, in combination with b₁), at least one component b₂) or b₃)

b₂) fungicidal active ingredients selected from among the azoles III.1. to III.18

1-[(2RS,4RS;2RS,4SR)-4-bromo-2-(2,4-dichlorophenyl)-tetrahydrofuryl]-1H-1,2,4-triazole (III.1)

2-(4-chlorophenyl)-3-cyclopropyl-1-(1H-1,2,4-triazol-1-yl)butan-2-ol (III.2)

(±)-4-chloro-4-[4-methyl-2-(1H-1,2,4-triazol-1-ylmethyl)-1,3-dioxolan-2-yl]phenyl 4-chlorophenylether (III.3)

(E)-(R,S)-1-(2,4-dichlorophenyl)-4,4-dimethyl-2-(1H-1,2,4-triazol-1-yl)pent-1-en-3-ol (III.4)

(z)-2-(1H-1,2,4-triazol-1-ylmethyl)-2-(4-fluorophenyl)-3-(2-chlorophenyl)oxirane (III.5)

4-(4-chlorophenyl)-2-phenyl-2-(1H-1,2,4-triazolylmethyl)butyronitrile (III.6)

3-(2,4-dichlorophenyl)-6-fluoro-2-(1H-1,2,4-triazol-1-yl)quinazolin-4(3H)-one (III.7)

bis(4-fluorophenyl)(methyl)(1H-1,2,4-triazol-1-ylmethyl)silane (III.8)

(R,S)-2-(2,4-dichlorophenyl)-1-(1H-1,2,4-triazol-1-yl)hexan-2-ol (III.9)

(1RS,5RS;1RS,5SR)-5-(4-chlorobenzyl)-2,2-dimethyl-1-(1H-1,2,4-triazol-1-ylmethyl)cyclopentanol (III.10)

N-propyl-N-[2-(2,4,6-trichlorophenoxy)ethyl]-imidazole-1-carboxamide (III.11)

(±)-1-[2-(2,4-dichlorophenyl)-4-propyl-1,3-dioxolan-2-ylmethyl]-1H-1,2,4-triazole (III.12)

(R,S)-1-(4-chlorophenyl)-4,4-dimethyl-3-(1H-1,2,4-triazol-1-ylmethyl)pentan-3-ol (III.13)

(±)-2-(2,4-dichlorophenyl)-3-(1H-1,2,4-triazolyl)propyl 1,1,2,2-tetrafluoroethyl ether (III.14)

(E)-1-[1-[[4-chloro-2-(trifluoromethyl)phenyl]imino]-2-propoxyethyl]-1H-imidazole (III.15)

(RS)-2,4'-difluoro-α-(1H-1,2,4-triazol-1-ylmethyl)benzhydryl alcohol (III.16)

2-p-chlorophenyl-2-(1H-1,2,4-triazol-1-ylmethyl)-hexylnitrile (III.17) and 1-(2,4-dichloro-β-propylphenethyl)-1H-1,2,4-triazole (III.18)

and/or b₃) benzoic esters of the formula IV

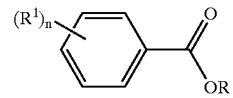

(IV)

where the substituents have the following meanings:

n has a value of 0 to 3

R is $C_1$–$C_8$-alkyl, $C_6$–$C_{14}$-aryl, $C_6$–$C_{14}$-aryl-$C_1$–$C_8$-alkyl, $R^1$ is hydrogen, $C_1$–$C_8$-alkyl, $C_6$–$C_{14}$-aryl, $C_6$–$C_{14}$-aryl-$C_1$–$C_8$-alkyl-, halogen, $C_1$–$C_6$-alkoxy, wherein the weight percentages of components (a) and (b) are based on the total weight og the multi-phase suspoemulsion.

2. The multi-phase suspoemulsion defined in claim 1, which comprises from 5 to 15% by weight of one or more of the ingredients of formulae III.9, III.12 and III.18.

3. The multi-phase suspoemulsion defined in claim 1, wherein the oil phase density of the components in emulsion b) ranges from 0.95 to 1.05 g/cm³.

4. The multi-phase suspoemulsion defined in claim 1, wherein component b is a mixture of one ingredient of formulae II.1 to II.5 and an azole selected from among III.9, III.12 and III.18 in a weight ratio of from 1.5:1 to 5:1.

5. A method for the treatment of timber against fungal timber pests, which comprises treating the timber with an active amount of the multi-phase suspoemulsion defined in claim 1, wherin the multiphase suspoemulsion is applied in a water diluted form.

6. A method for protection of plants against harmful fungi, which comprises treating the plants or the fungi with an effective amount of the multi-phase suspoemulsion defined in claim 1, wherein the multiphase suspoemulsion is applied in a water diluted form.

* * * * *

UNITED STATES PATENT AND TRADEMARK OFFICE
CERTIFICATE OF CORRECTION

PATENT NO. : 6,558,685 B1
DATED : May 6, 2003
INVENTOR(S) : Kober et al.

It is certified that error appears in the above-identified patent and that said Letters Patent is hereby corrected as shown below:

Column 16,
Line 49, "I.1" should be -- II.1 --.

Column 18,
Line 29, "og the" should be -- of the --.

Signed and Sealed this

Twenty-sixth Day of August, 2003

JAMES E. ROGAN
*Director of the United States Patent and Trademark Office*